US00PP22073P2

(12) United States Plant Patent
Klemm et al.

(10) Patent No.: US PP22,073 P2
(45) Date of Patent: Aug. 9, 2011

(54) ***OSTEOSPERMUM* PLANT NAMED 'KLEOE09176'**

(50) Latin Name: ***Osteospermum ecklonis* Norl.**
Varietal Denomination: KLEOE09176

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,135

(22) Filed: Mar. 30, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt
(74) *Attorney, Agent, or Firm* — Jondle & Associates, P.C.

(57) ABSTRACT

An *Osteospermum* variety named 'KLEOE09176' particularly distinguished by a very early flowering time, large, dusty white and violet-colored flowers, continuous flowering from early Spring to Fall, and excellent branching, is disclosed.

1 Drawing Sheet

Genus and species: *Osteospermum ecklonis* Norl.
Variety denomination: 'KLEOE09176'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE09176'. The new variety originated from an open pollination made in September 2006 in Stuttgart, Germany. The female parent was a proprietary *Osteospermum* plant named 'OE 2006 108' (unpatented), and the male parent was an unknown *Osteospermum* plant (unpatented).

The new variety was first propagated via vegetative cuttings in May 2007 in Stuttgart, Germany and has been asexually reproduced repeatedly by vegetative cuttings in Stuttgart, Germany for approximately 10 generations. The present invention has been found to retain its distinctive characteristics through successive asexual propagations via vegetative cuttings.

Plant Breeder's Rights for this variety have not been applied for. 'KLEOE09176' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. A very early flowering time;
2. Large, dusty white and violet-colored flowers;
3. Continuous flowering from early Spring to Fall; and
4. Excellent branching.

DESCRIPTION OF THE PHOTOGRAPH

This new *Osteospermum* plant is illustrated by the accompanying photograph which shows a close-up of a flower of the plant. The colors shown are as true as can be reasonably obtained by conventional photographic procedures. The photograph was taken in Summer 2009 of a 7-month-old plant in the field in Stuttgart, Germany, under conditions which approximate those generally used in commercial practice.

DESCRIPTION OF THE NEW VARIETY

The following detailed descriptions set forth the distinctive characteristics of 'KLEOE09176'. The data which define these characteristics were collected from asexual reproductions carried out in Stuttgart, Germany. The plant history was taken in Summer 2009 on 7-month-old plants which were potted at 4 weeks in 12 centimeter containers and then planted in the ground in calendar week 20. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Asteraceae.
- *Botanical name.*—*Osteospermum ecklonis* Norl.
- *Common name.*—African daisy.

Parentage:
- *Female parent.*—A proprietary *Osteospermum* plant named 'OE 2006 108' (unpatented).
- *Male parent.*—An unknown *Osteospermum* plant (unpatented).

Plant:
- *Form and habit.*—Semi-upright (V-shape).
- *Growth habit.*—Compact.
- *Branching habit.*—Excellent branching.
- *Height (from top of soil, including inflorescence).*—45.0 cm.
- *Width (including inflorescences).*—50.0 cm.
- *Propagation.*—Vegetative cuttings.
- *Time to produce a finished flowering plant.*—15 weeks.
- *Time to initiate and develop roots.*—4 weeks.
- *Root description.*—Freely rooting.

Leaves:
*Arrangement.*—Alternate.
*Shape.*—Obovate.
*Apex.*—Acute.
*Base.*—Acute.
*Margin.*—Serrate.
*Color.*—Immature leaf: Upper surface: RHS 137B. Lower surface: RHS 137C. Mature leaf: Upper surface: RHS 137A. Lower surface: RHS 137B.
*Length.*—6.0 cm.
*Width.*—2.0 cm.
*Texture.*—Glabrous on the upper surface.
*Appearance.*—Leathery on the upper surface.
*Petioles.*—Absent.
*Venation pattern.*—No venation.

Stems:
*Total number of branches.*—9.
*Length.*—40.0 cm to 45.0 cm.
*Diameter.*—0.5 cm to 1.0 cm.
*Internode length.*—1.0 cm to 2.7 cm.
*Color.*—RHS 146D.
*Texture.*—Glabrous.
*Appearance.*—Leathery.
*Anthocyanin.*—Absent.

Inflorescence buds:
*Shape.*—Oval to round.
*Length.*—1.0 cm to 1.5 cm.
*Diameter.*—1.0 cm.
*Color* (*at tight bud just before the ray florets unfold*).—RHS 143B.

Inflorescence:
*Type.*—Composite, single.
*Blooming habit.*—Plants flower continuously from early Spring to Fall.
*Quantity of inflorescences per plant.*—90 to 100.
*Lastingness of the inflorescences on the plant.*—10 days.
*Fragrance.*—Absent.
*Inflorescence diameter.*—5.0 cm to 6.0 cm.
*Inflorescence depth.*—Approximately 1.5 cm.
*Disc diameter.*—1.5 cm.

Disc floret:
*Quantity per inflorescence.*—Approximately 50.
*Shape.*—Tubular, radially symmetrical.
*Tube color.*—Closed: RHS 98A. Mature: RHS 98B.
*Length.*—Approximately 0.7 cm.
*Diameter* (*at apex*).—0.2 cm to 0.3 cm.
*Apex.*—Acuminate.
*Apex color.*—RHS 98B.
*Base.*—Obtuse.
*Base color.*—RHS 2D.
*Margin.*—Entire.

Ray floret:
*Quantity per inflorescence.*—16 to 17.
*Shape.*—Obovate.
*Color.*—Upper surface: RHS N155B and RHS 77C. Lower surface: RHS 12B and RHS 176B and RHS 164C.
*Length.*—3.0 cm.
*Width.*—0.7 cm.
*Apex.*—Obtuse.
*Base.*—Acute.
*Margin.*—Entire.
*Texture.*—Velvety.
*Peduncle.*—Length: 9.0 cm. Diameter: 0.2 cm. Texture: Rough. Color: RHS 146B.

Phyllaries:
*Arrangement.*—Single.
*Observed quantity per plant.*—16 to 17.
*Shape.*—Lanceolate.
*Color.*—Upper surface: RHS 143A to RHS 143C (stripes). Lower surface: RHS 143D and RHS 141D (stripes).
*Length.*—0.8 cm to 1.2 cm.
*Width.*—0.1 cm to 0.2 cm.
*Apex.*—Acute.
*Base.*—Obtuse.
*Margin.*—Entire.
*Texture.*—Rough.

Reproductive organs:
*Androecium.*—Location: In the disc floret. Stamens: Quantity: Numerous. Shape: Tubular. Color: Top: RHS 93A. Middle: RHS 160D. Base: RHS 157D. Filament length: 0.5 cm to 0.9 cm. Filament diameter: 0.1 cm to 0.2 cm. Anther: Shape: Longitudinal. Color: RHS 186A. Length: 0.2 cm. Diameter: 0.02 cm. Pollen: Color: RHS 162A. Amount: Sparse.
*Gynoecium.*—Location: At the face of the ray floret. Pistils: Number: 16 to 17. Length: 0.3 cm to 0.4 cm. Diameter: 0.03 cm. Stigma: Color: RHS 202A. Shape: Ovate. Length: 0.07 cm to 0.1 cm. Diameter: 0.002 cm. Style: Color: RHS 186A. Length: 0.3 cm to 0.5 cm. Diameter: 0.001 cm.

Fruit and seed set: Double, brown, torpedo-shaped seeds; abundant seed set observed.

Disease and insect resistance: No particular disease or insect resistance observed.

COMPARISON WITH PARENTAL AND COMMERCIAL VARIETIES

'KLEOE09176' differs from the female parent, the proprietary *Osteospermum* plant named 'OE 2006 108' (unpatented), in that 'KLEOE09176' has dusty white and violet-colored flowers, whereas 'OE 2006 108' has pink sand-colored flowers. In addition, 'KLEOE09176' has a more compact growth habit and better branching than 'OE 2006 108'.

'KLEOE09176' differs from the commercial variety 'KLEO03106' (unpatented) in that 'KLEOE09176' has an earlier flowering time and better branching than 'KLEO03106'.

We claim:

1. A new and distinct variety of *Osteospermum* plant named 'KLEOE09176' as shown and described herein.

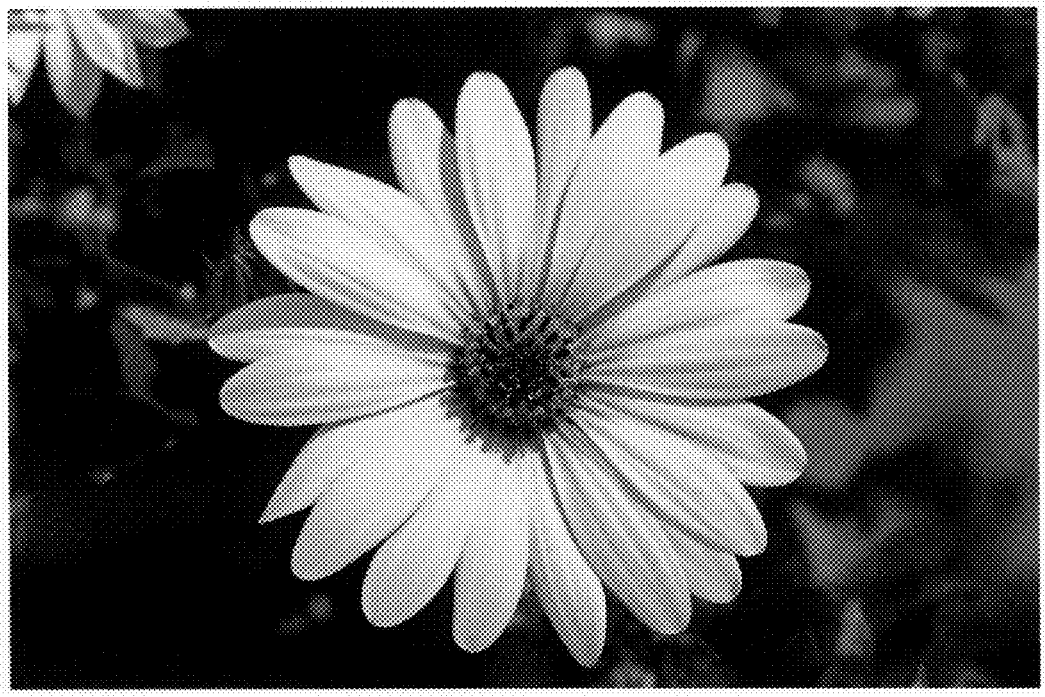

* * * * *